United States Patent [19]

Huang et al.

[11] Patent Number: 5,032,405
[45] Date of Patent: Jul. 16, 1991

[54] ORAL PHARMACEUTICAL COMPOSITION FOR ACID SENSITIVE PROTEINACEOUS AGENTS

[75] Inventors: Hua-pin Huang, Succasunna; Isaac Ghebre-Sellassie, Stanhope; Mahdi B. Fawzi, Flanders, all of N.J.

[73] Assignee: Warner-Lambert Company, Morris Plains, N.J.

[21] Appl. No.: 413,197

[22] Filed: Sep. 27, 1989

[51] Int. Cl.$^5$ .................. A61K 9/48; A61K 37/00
[52] U.S. Cl. ..................... 424/463; 424/88; 424/89; 424/465; 424/474; 424/482; 424/489; 424/494; 424/93; 514/888
[58] Field of Search ............ 424/463, 89, 465, 482

[56] References Cited

U.S. PATENT DOCUMENTS

| | | | |
|---|---|---|---|
| 3,767,790 | 10/1973 | Guttag | 424/81 |
| 3,870,598 | 3/1975 | Aleseeva et al. | 424/89 |
| 4,102,999 | 7/1978 | Umezawa et al. | 424/123 |
| 4,337,242 | 6/1982 | Markus et al. | 424/89 |
| 4,397,844 | 8/1983 | Baschang et al. | 260/112.5 R |
| 4,710,378 | 12/1987 | Ohtomo et al. | 424/89 |
| 4,870,059 | 9/1989 | Mitsuhashi et al. | 514/53 |

FOREIGN PATENT DOCUMENTS

| | | |
|---|---|---|
| 117250 | 1/1976 | German Democratic Rep. |
| 86/06635 | 11/1986 | PCT Int'l Appl. |
| 8300435 | 2/1983 | United Kingdom ............ 424/463 |
| 2166349 | 5/1986 | United Kingdom. |

*Primary Examiner*—Thurman Page
*Assistant Examiner*—James M. Spear
*Attorney, Agent, or Firm*—Mathews, Woodbridge & Collins, P.A.

[57] ABSTRACT

An orally administrable formulation of a biologically active, acid sensitive, proteinaceous agent comprises a composition of a lyophilized mixture of the proteinaceous agent and maltose, optionally with a particulate diluent. This composition is then uniformly coated with an alkaline-soluble polymeric film containing at least one partially esterified polymethacrylic acid as a major component.

11 Claims, No Drawings

ORAL PHARMACEUTICAL COMPOSITION FOR ACID SENSITIVE PROTEINACEOUS AGENTS

The present invention relates to orally administrable formulations for biologically active proteinaceous agents which are acid sensitive.

Proteinaceous materials such as polypeptides and glucoproteins constitute a large segment of pharmacologically active agents available to the physician. Such materials include hormones such as insulin, ACTH, TSH, STH, calcitonin, antibiotics such as interferon, enzymes such as Factor VIII, and immunological agents such as vaccines, toxin/antitoxins, toxoids, and globulins, to name but a few. By reason of their sensitivity to hydrolysis, many of these agents cannot be administered by the oral route and moreover have only limited stability even under normal conditions.

Since this instability is chemical in nature and not a function of the specific pharmacological activity exhibited, the following description will utilize vaccines, and in particular influenza vaccine, as representative.

The membrane-like envelope of the influenza virus contains two glycoproteins, hemagglutinin and neuraminidase, which constitute the two main immunogenic components of influenza vaccines. Whole virion vaccines are derived from influenza virus grown in embryonated chicken eggs. The virus is harvested from the allantoic fluid and chemically inactivated with formaldehyde or β-propiolactone. Subvirion vaccines then are obtained by disrupting the virus particle with detergents or organic solvents.

Influenza vaccine normally is administered intramuscularly through the deltoid muscle. This route of administration can produce adverse reactions such as soreness, diarrhea, hypersensitivity, etc. Moreover while relatively stable at normal pHs, i.e., from 6 to 8, the vaccines are inactivated when subjected to pH values below about 5. Similarly, if the temperature is raised above about 45° C., the vaccines become inactivated in a matter of hours (or even minutes, at higher temperatures). Simple lyophilization also can produce a significant loss of activity, as will solvents precipitation with ethanol or acetone.

Various attempts to overcome the sensitivity problems associated with proteinaceous materials have been proposed. UK Patent Specification 2,166,349 claims a vaccine formulated in an enteric coated dosage form. U.S. Pat. Nos. 3,860,490 and 3,767,790 disclose the entrapment of influenza vaccine in hydrophilic polyacrylates or polymethacrylates to provide controlled release formulations. U.S. Pat. No. 4,397,844 discloses the formation of chemical derivatives of antigens, including derivatives of influenza vaccine, which are said to produce an increase in immunoresponse and which are formulated with solid excipients to make tablets or tablet cores. EP-A 86/06635 discloses a complex of an immunogen to interact with the mucosal ephithelium upon oral administration. While not formulated for oral administration, U.S. Pat. No. 3,870,598 discloses the use of peptone to stabilize a vaccine before lyophilization. Peptone or sucrose also are described lyophilization stabilizers in DL 117,250.

Very briefly, the present invention involves a composition of a lyophilized mixture of the proteinaceous agent and maltose. This composition then is uniformly coated with an alkaline-soluble polymeric film comprising at least one partially esterified polymethacrylic acid as a major component. Preferably the lyophilized mixture contains a particulate diluent in addition to the proteinaceous agent and maltose.

Maltose, a nonhygroscopic disaccharide, serves to protect the protein during and after lyophilization. While sucrose also can be used for this purpose, it tends to be overly hygroscopic. Other substances including polyethylene glycol (4000), inulin, PVP, glucose, mannitol, starch, dextran, etc. are generally not suitable, a decrease in activity being observed following lyophilization.

Typically the ratio of vaccine to maltose will be from about 1:100 to about 1:10,000 on a weight basis, preferably from about 100 to about 1000.

Although maltose also serves as a diluent, it often is desirable to include a further particulate diluent with the vaccine and maltose in order to improve powder flowability. This component can be a cellulose derivative, mannitol, lactose, magnesium carbonate, magnesium oxide, calcium carbonate, calcium sulfate, dibasic calcium phosphate, bentonite, silica gel, talc, or starch. Surprisingly when used alone, a number of these materials such as cellulose and lactose will decrease the activity of the vaccine upon lyophilized. Such a decrease is not observed if maltose is present together with the protein and particulate diluent.

The preferred particulate diluent is a cellulose, particularly microcrystalline cellulose. Typically the ratio of vaccine to particulate diluent will be from about 1:900 to about 1:1500 on a weight basis, preferable from about 1:1100 to about 1:1300.

The components are mixed and then lyophilized utilizing conventional freeze drier equipment, as for example a Consol 12, available from Vir Tis Co., Gardiner, New York. The free flowing lyophilized composition then is formulated as an orally administrable formulation and as capsules, granules, or tablets. Thus the free flowing lyophilized composition is converted to granules, compressed into tablets, or introduced into a conventional capsule shell.

While the foregoing pharmaceutical composition maintains a high degree of biological activity when analyzed in vitro and exhibits improved stability, it is still not effective orally since it is rapidly inactivated by the acidic environment of the stomach.

Moreover, the absorption of proteins in the gastrointestinal tract appears to be centered in the lower portion of the ileum at the gut-associated lymphatic system or "Peyer's patches". [See Caldwell et al., J. Pharm. Pharmacol., 34, 520 (1982).] It is possible with the present invention to target the proteinaceous material to this area.

To achieve these objectives, the pharmaceutical formulation is uniformly coated with a specific alkaline-soluble polymeric film. The pH at which the film will dissolve is primarily a function of the ratio of esterified carboxy groups to unesterified carboxy groups. For purposes of the present invention, polymers having a ratio of esterified carboxy groups to unesterified carboxy groups of from about 2:1 to about 1:1 and a mean molecular weight of from 130,000 to 140,000 are suitable.

Preferably the film contains at least one partially methylated polymethacrylic acid which is soluble above a pH about 7. To attain this parameter, the polymer should have a ratio of esterified carboxy groups to unesterified carboxy groups of about 2:1.

The inherent pH at which a film of this polymer will dissolve then can be controlled through incorporation of a second polymer having a lower ratio of esterified carboxy groups to unesterified carboxy groups. In this embodiment, the first partially methylated polymethacrylic acid is combined with lesser amounts of a second partially methylated polymethacrylic acid soluble in an aqueous media at a pH above about 6. This second polymer, for example, can have a ratio of esterified carboxy groups to unesterified carboxy groups of about 1:1. Both the first and second polymers will have mean molecular weights of about 135,000.

The pH at which the resultant film dissolves, and the subsequent availability of the proteinaceous material for absorption, can thus be controlled by the relative proportions of two partially methylated polymethacrylic acids, each of which has a different ratio of esterified carboxy groups to unesterified carboxy groups.

Evaluation of the activity of the vaccine utilized herein can be accomplished utilizing the following technique.

A 5 mL Guinea pig blood sample (obtained by cardiac puncture under anesthesia) is mixed immediately with 0.5 mL of 5% sodium citrate solution and the red blood cells collected by centrifugation at 1500 RPM for 10 minutes. A 10% stock solution of the collected red blood cells in buffered saline (pH 7.0, 0.85% NaCl, 0.08% $Na_2HPO_4$, and 0.03% $NaH_2PO_4$) then is prepared and stored at 4° C. for use within a week. Serial two-fold dilutions of a 0.1mL vaccine sample are prepared from buffered saline. A 0.5% suspension is prepared by mixing 5mL of the stock solution of red blood cells in 100 mL of buffered saline and 0.1 mL aliquots are combined with the 0.1 mL diluted vaccine preparations. After standing at room temperature for two hours, sedimented red blood cells are observed and the end point determined as the highest dilution showing hemagglutination.

The following examples will serve to further illustrate the invention.

EXAMPLE 1

In a dry room and under low humidity conditions, maltose (5 g) is mixed with 100 mL of a commercial aqueous influenza vaccine suspension containing 208 μg/mL of vaccine and 20 g. of microcrystalline cellulose. This mixture is then lyophilized in a Consol 12 freeze drier (Vir Tis Co., Gardiner, New York).

Two hundred milligrams of the lyophilized product are introduced into a #1 gelatin capsule. A coating solution is prepared from an ethanolic solution of (i) 1.6 g of a partially methylated polymethacrylic acid having a ratio of esterified carboxy groups to unesterified carboxy groups of about 2:1 and a mean molecular weight of about 135,000 (Eudragit S), (ii) 2.4 g of a partially methylated polymethacrylic acid having a ratio of esterified carboxy groups to unesterified carboxy groups of about 1:1 and a mean molecular weight of about 135,000 (Eudragit L) and (iii) 0.8 mL of plasticizer (dibutyl phthalate). Groups of approximately 40 capsules are then coated in an Aeromatic fluid-bed drier with the foregoing coating solution. Assay (see above) showed no loss of activity as compared to starting vaccine. In comparison, a combination of the vaccine and microcrystalline cellulose demonstrated only 10% activity while a combination of the vaccine and lactose demonstrated only 25% activity.

What is claimed is:

1. An orally administrable formulation of a biologically active, hormone, antibiotic, or immunological agent which comprises (a) a composition of a lyophilized mixture comprising (i) the hormone, antibiotic, or immunological agent, (ii) maltose and (iii) a particulate diluent, said composition being uniformly coated with (b) an alkaline-soluble polymeric film comprising at least one partially esterified polymethacrylic acid as a major component.

2. An or administrable formulation according to claim 1 wherein said particulate diluent is a cellulose, mannitol, lactose, magnesium carbonate, magnesium oxide, calcium carbonate, calcium sulfate, dibasic calcium phosphate, bentonite, silica gel, talc, or starch.

3. An orally administrable formulation according to claim 2 wherein said particulate diluent is a cellulose.

4. An orally administrable formulation according to claim 3 wherein said particulate diluent is microcrystalline cellulose.

5. An orally administrable formulation according to claim 1 wherein said alkaline-soluble polymeric film comprises at least one partially methylated polymethacrylic acid having a mean molecular weight of from 130,000 to 140,000 with a ratio of esterified carboxy groups to unesterified carboxy groups of from about 2:1 to about 1:1.

6. An orally administrable formulation according to claim 1 wherein said film comprises a first partially methylated polymethacrylic acid soluble in an aqueous media at a pH above about 7 and having a mean molecular weight of about 135,000 with a ratio of esterified carboxy groups to unesterified carboxy groups of about 2:1.

7. An orally administrable formulation according to claim 6 wherein said film comprises said first partially methylated polymethacrylic acid in combination with a second partially methylated polymethacrylic acid soluble in an aqueous media at a pH above about 6 and having a mean molecular weight of about 135,000 with a ratio of esterified carboxy groups to unesterified carboxy groups of about 1:1.

8. An orally administrable formulation according to claim 1 wherein said acid sensitive proteinaceous agent is a vaccine.

9. An orally administrable formulation according to claim 8 wherein said acid sensitive proteinaceous agent is an influenza vaccine.

10. An orally administrable formulation of an influenza vaccine which comprises a capsule containing (a) a composition of a lyophilized mixture of (i) the influenza vaccine, (ii) maltose, and (iii) microcrystalline cellulose, said capsule being uniformly coated with (b) a film comprising as a major component a partially methylated polymethacrylic acid soluble in an aqueous media at a pH above about 7 and having a mean molecular weight of about 135,000 with a ratio of esterified carboxy groups to unesterified carboxy groups of about 2:1.

11. An orally administrable formulation according to claim 10 wherein said film comprises said partially methylated polymethacrylic acid in combination with a second partially methylated polymethacrylic acid soluble in an aqueous media at a pH above about 6 and having a mean molecular weight of about 135,000 with a ratio of esterified carboxy groups to unesterified carboxy groups of about 1:1.

* * * * *